(12) United States Patent
Sharps et al.

(10) Patent No.: US 8,960,014 B2
(45) Date of Patent: Feb. 24, 2015

(54) METHODS OF VALIDATING EDGE STRENGTH OF A GLASS SHEET

(71) Applicants: Robert Wendell Sharps, Corning, NY (US); Todd Marshall Wetherill, Painted Post, NY (US)

(72) Inventors: Robert Wendell Sharps, Corning, NY (US); Todd Marshall Wetherill, Painted Post, NY (US)

(73) Assignee: Corning Incorporated, Corning, NY (US)

(*) Notice: Subject to any disclaimer, the term of this patent is extended or adjusted under 35 U.S.C. 154(b) by 244 days.

(21) Appl. No.: 13/624,265

(22) Filed: Sep. 21, 2012

(65) Prior Publication Data

US 2014/0083198 A1 Mar. 27, 2014

(51) Int. Cl.
*G01N 3/08* (2006.01)

(52) U.S. Cl.
USPC .............................................. 73/834; 73/760

(58) Field of Classification Search
CPC ........... G01N 3/20; G01N 3/08; G01N 25/00; G01N 33/386
USPC .......................................... 73/760, 834, 853
See application file for complete search history.

(56) References Cited

U.S. PATENT DOCUMENTS

| | | | | |
|---|---|---|---|---|
| 4,395,917 A | * | 8/1983 | Maltby et al. .................... | 73/840 |
| 4,440,559 A | * | 4/1984 | Shaw, Jr. ......................... | 65/99.5 |
| 4,711,697 A | * | 12/1987 | Kaukler ........................... | 356/30 |
| 5,311,276 A | * | 5/1994 | Masao et al. ................ | 356/239.1 |
| 5,676,722 A | | 10/1997 | Seidel .............................. | 65/111 |
| 6,004,655 A | | 12/1999 | Tanaka et al. .................. | 428/192 |
| 6,501,546 B1 | | 12/2002 | Weiss .......................... | 356/239.1 |
| 6,515,441 B1 | * | 2/2003 | Tyckowski et al. ........... | 318/445 |
| 6,535,824 B1 | * | 3/2003 | Mansky et al. ..................... | 506/8 |
| 6,796,144 B2 | * | 9/2004 | Shepard et al. .............. | 65/29.11 |
| 7,746,440 B2 | | 6/2010 | Liu et al. ....................... | 349/153 |
| 8,030,589 B2 | * | 10/2011 | Huber et al. .................. | 209/578 |
| 8,571,615 B2 | * | 10/2013 | Hays ............................. | 505/191 |
| 2003/0076487 A1 | | 4/2003 | Cannon et al. .................. | 356/33 |
| 2008/0202167 A1 | | 8/2008 | Cavallaro et al. ............... | 65/104 |
| 2010/0107848 A1 | | 5/2010 | Joseph, II et al. .............. | 83/862 |

(Continued)

FOREIGN PATENT DOCUMENTS

CN 201010558344 A 11/2010
CN 102072918 5/2011

(Continued)

OTHER PUBLICATIONS

S. Gulati and J. Helfinstine, Edge strength testing of thin glasses, Inter. J. Appl. Glass Sci., 2, 39-46, 2011.
W. Dalgliesh and D. Taylor, The strength and testing of window glass, Canadian J. Civil Eng., 17, 752-762, 1990.
C. Pantelides, G. Sallee and J. Minor, Edge strength of window glass by mechanical test, J. Eng. Mech., 120, 1076-1090, 1994.

(Continued)

*Primary Examiner* — Max Noori
(74) *Attorney, Agent, or Firm* — Kevin M. Able

(57) ABSTRACT

Methods of validating edge strength of a glass sheet are provided. The glass sheet includes a first surface, a second surface opposing the first surface, a thickness defined between the first surface and the second surface, and at least one edge including an edge surface. The first surface and the second surface intersect the edge surface of the at least one edge. The methods include a step (I) of noncontactually thermally loading the glass sheet to subject at least a portion of the at least one edge to a tensile stress. The methods also include a step (II) of determining whether the at least one edge has an edge strength below a predetermined level by detecting whether a resulting strength imperfection has originated in the glass sheet due to the noncontactual thermal loading of step (I).

20 Claims, 12 Drawing Sheets

(56) References Cited

U.S. PATENT DOCUMENTS

2012/0040146 A1    2/2012   Garner et al. .............. 428/192
2012/0065072 A1*   3/2012   Hays .......................... 505/162
2012/0135195 A1    5/2012   Glaesemann et al. ...... 428/156

FOREIGN PATENT DOCUMENTS

EP          0878702 B1      3/2004
JP          2011/112587 A   6/2011
JP          2012/078132 A   4/2012

OTHER PUBLICATIONS

M. Inoue, T. Ono and I. Sato, Evaluation of strength and edge flaw severity of barium borosilicate glass substrate by thermal downshock testing, J. Cer. Soc. Japan, 101, 149-153, 1993.

O. Gaume and R. Gy, Measurement of edge strength using a special thermal test, Proc. Inter. Cong. Glass, 20, 1-6, 2004.

ASTM International, Standard Specification for Flat Glass, C 1036-06.

R. Roark, Formulas for Stress and Strain, 4th Ed., McGraw-Hill, 1965.

* cited by examiner

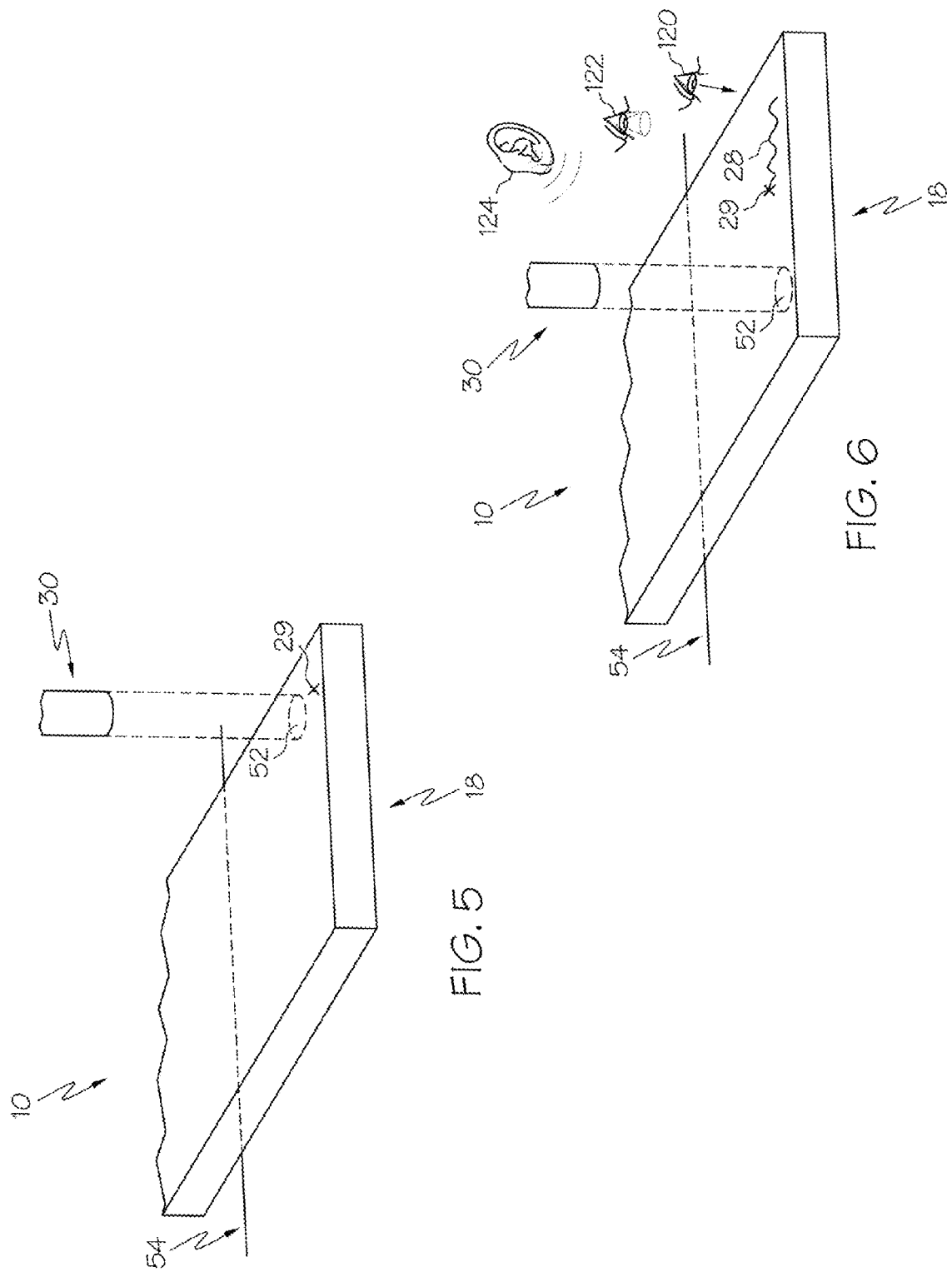

METHODS OF VALIDATING EDGE STRENGTH OF A GLASS SHEET

FIELD

The present invention relates generally to methods of validating edge strength and, more particularly, to methods of validating edge strength of a glass sheet.

BACKGROUND

Glass sheets are component in products such as architectural and automotive windows, liquid crystal display (LCD) modules, and photovoltaic (PV) panels. For these applications, a glass sheet is typically cut to size, and then resulting sharp edges of the glass sheet are beveled by grinding and polishing. Cutting, edge machining, and other processing steps can introduce initial flaws, such as chips or cracks, at surfaces and edges of the glass sheet. Strength imperfections can originate from the initial flaws when the glass sheet is subject to tensile stress. Accordingly, initial flaws can compromise the strength of the glass sheet.

SUMMARY

The following presents a simplified summary of the disclosure in order to provide a basic understanding of some example aspects described in the detailed description.

In a first aspect, a method of validating edge strength of a glass sheet is provided. The glass sheet comprises a first surface, a second surface opposing the first surface, a thickness defined between the first surface and the second surface, and at least one edge comprising an edge surface. The first surface and the second surface intersect the edge surface of the at least one edge. The method comprises a step (I) of noncontactually thermally loading the glass sheet to subject at least a portion of the at least one edge to a tensile stress. The method also comprises a step (II) of determining whether the at least one edge has an edge strength below a predetermined level by detecting whether a resulting strength imperfection has originated in the glass sheet due to the noncontactual thermal loading of step (I).

In one example of the first aspect, the tensile stress is a hoop stress.

In another example of the first aspect, step (I) comprises producing at least one temperature gradient in the glass sheet.

In still another example of the first aspect, step (I) comprises producing at least one temperature gradient in the glass sheet, the temperature gradient emanating from a site on the glass sheet, the site being a distance from the edge surface.

In yet another example of the first aspect, step (I) comprises producing at least one temperature gradient in the glass sheet, the temperature gradient emanating from a site on the glass sheet, the site having a position that changes based on translational motion of the glass sheet relative to a source of the noncontactual thermal loading.

In a further example of the first aspect, step (I) comprises delivering at least one focused infrared beam to at least one of the first and second surfaces of the glass sheet, the beam producing at least one temperature gradient in the glass sheet.

In another example of the first aspect, step (I) comprises delivering (i) at least a first focused infrared beam to the first surface of the glass sheet and (ii) at least a second focused infrared beam to the second surface of the glass sheet, the at least first and second focused beams forming at least one pair of beams that are coincident with respect to the glass sheet.

In still another example of the first aspect, during step (I) all of the at least one edge is progressively subjected to the tensile stress based on translational motion of the glass sheet relative to a source of the noncontactual thermal loading.

In yet another example of the first aspect, the at least one edge comprises at least a first edge and a second edge opposing the first edge, and further wherein step (I) comprises independently noncontactually thermally loading the glass sheet to subject at least a portion of the first edge and at least a portion of the second edge to the tensile stress.

In a further example of the first aspect, the at least one edge comprises a complete perimeter of the glass sheet, and further wherein step (I) comprises noncontactually thermally loading the glass sheet to subject the complete perimeter to the tensile stress.

In still a further example of the first aspect, step (I) comprises delivering at least one focused jet of gas to at least a portion of the at least one edge, the gas being colder than the at least one edge, the gas producing at least one temperature gradient in the glass sheet.

In yet a further example of the first aspect, during step (II) the detecting of the resulting imperfection comprises a detection method selected from the group consisting of visual detection, optical detection, and acoustic detection.

In another example of the first aspect, the method further comprises a step (III) of estimating the tensile stress based on an interference fit model of a heated inner cylinder and a non-heated outer cylinder, wherein: the inner cylinder corresponds to a site on the glass sheet from which a temperature gradient emanates and has an inner ring radius; the outer cylinder corresponds to a portion of the glass sheet surrounding the site and comprises an outer edge that intersects the at least one edge of the glass sheet and has an outer ring radius; the inner and outer cylinders being concentric and made from the glass sheet, in accordance with the equation:

$$s_t = +\Delta T \alpha E (a^2/b^2)$$

in which $s_t$ is the tangential stress at the outer edge of the outer cylinder; $\Delta T$ is the temperature difference between the inner cylinder and the outer cylinder; $\alpha$ is the coefficient of thermal expansion of the glass sheet; E is the Young's modulus for the glass sheet; a is the inner ring radius of the inner cylinder; and b is the outer ring radius of the outer cylinder.

In still another example of the first aspect, the method further comprises a step of shaping the at least one edge of the glass sheet prior to steps (I) and (II), wherein the glass sheet is of a predetermined size.

In yet another example of the first aspect, the method further comprises a step of chemically strengthening the glass sheet prior to steps (I) and (II).

In a further example of the first aspect, the thickness defined between the first surface of the glass sheet and the second surface of the glass sheet is less than about 1 mm.

The first aspect may be carried out alone or in combination with any one or more of the examples of the first aspect discussed above.

In a second aspect, a method of validating edge strength of a glass sheet is provided wherein the glass sheet includes a first surface, a second surface opposing the first surface, a thickness defined between the first surface and the second surface, and at least one edge comprising an edge surface, wherein the first surface and the second surface intersect the edge surface of the at least one edge. The method comprises a step (I) of noncontactually thermally loading the glass sheet to produce at least one temperature gradient in the glass sheet. The temperature gradient emanates from a site on the glass sheet located a distance from the edge surface. The site has a position that changes based on translational motion of the glass sheet relative to a source of the noncontactual thermal loading. The temperature gradient subjects at least a portion of the at least one edge to a tensile stress. The method further includes a step (II) of determining whether the at least one edge has an edge strength below a predetermined level by detecting whether a resulting strength imperfection has originated in the glass sheet due to the noncontactual thermal loading of step (I).

In one example of the second aspect, step (I) comprises delivering at least one focused infrared beam to at least one of the first and second surfaces of the glass sheet, the beam producing at least one temperature gradient in the glass sheet.

In another example of the second aspect, step (I) comprises delivering (i) at least a first focused infrared beam to the first surface of the glass sheet and (ii) at least a second focused infrared beam to the second surface of the glass sheet, the at least first and second focused beams forming at least one pair of beams that are coincident with respect to the glass sheet.

In still another example of the second aspect, step (I) comprises delivering at least one focused jet of gas to at least a portion of the at least one edge, the gas being colder than the at least one edge, the gas producing at least one temperature gradient in the glass sheet.

The second aspect may be carried out alone or in combination with any one or more of the examples of the second aspect discussed above.

BRIEF DESCRIPTION OF THE DRAWINGS

These and other features, aspects and advantages of the present disclosure are better understood when the following detailed description is read with reference to the accompanying drawings, in which:

FIG. 5 is a schematic perspective view of part of an example glass sheet in translational motion, on a conveyor, relative to a source of noncontactual thermal loading;

FIG. 6 is a schematic perspective view similar to FIG. 5 but further demonstrating a step of detecting whether a resulting strength imperfection has originated in the glass sheet due to a noncontactual thermal loading;

DETAILED DESCRIPTION

Figure 1:
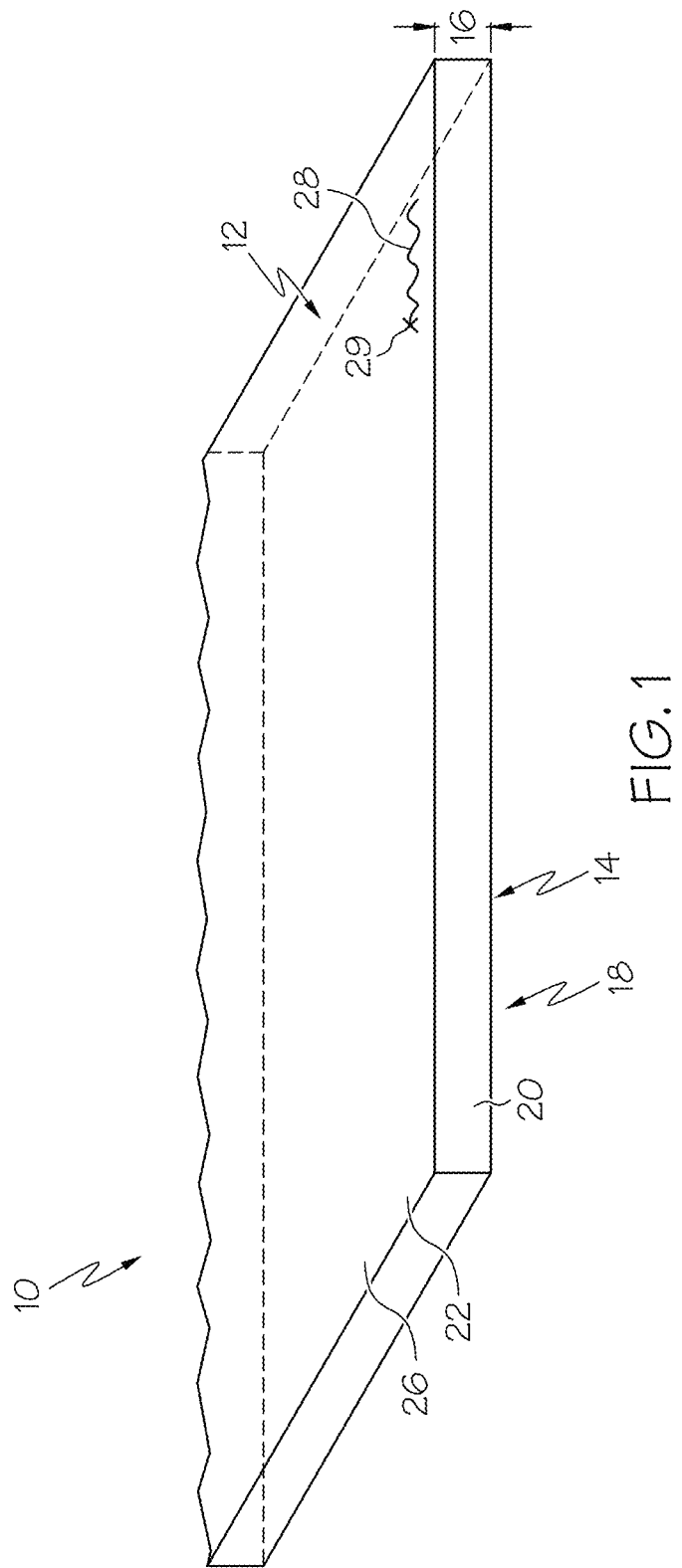
FIG. 1 is a schematic perspective view of part of an example glass sheet.

Methods will now be described more fully hereinafter with reference to the accompanying drawings in which example embodiments of the disclosure are shown. Whenever possible, the same reference numerals are used throughout the drawings to refer to the same or like parts. However, this disclosure may be embodied in many different forms and should not be construed as limited to the embodiments set forth herein.

Example methods of the disclosure will be described with initial reference to the glass sheet 10 illustrated in FIG. 1. The glass sheet 10 can comprise a first surface 12, a second surface 14 opposing the first surface 12, a thickness 16 defined between the first surface 12 and the second surface 14, and at least one edge 18 comprising an edge surface 20, wherein the first surface 12 and the second surface 14 intersect the edge surface 20 of the at least one edge 18. The glass sheet 10 can be made, for example, from soda-lime float glass or a specialty glass sheet. The glass sheet 10 can be, for example, a window glass sheet, an architectural glass sheet, an automotive glass sheet, an LCD glass sheet, or a photovoltaic panel glass sheet. Among LCD glass sheets, the glass sheet 10 can be, for example, a CORNING® EAGLE XG™ AMLCD glass sheet, a CORNING® EAGLE XG™ Slim glass sheet, a CORNING® WILLOW™ glass sheet, or a CORNING® LOTUS™ glass sheet. The glass sheet 10 can be, for example, a stock glass sheet, e.g. a glass sheet ordered in a size intended to be cut to create a final size, or a cut size glass sheet, e.g. a glass sheet cut to a predetermined size, such as a final intended size. Thus, for example, the glass sheet 10 can be a glass sheet that has been initially cut to size by a process including scoring, such as mechanical scoring, laser scoring, or the like, followed by separation. The glass sheet 10 can also be a glass sheet for which at least one edge thereof has been shaped and/or can be of a predetermined size. The glass sheet 10 can also be, for example a glass sheet that has been chemically strengthened, e.g. CORNING® GORILLA® Glass. The thickness 16 defined between the first surface 12 of the glass sheet 10 and the second surface 14 of the glass sheet 10 can be, for example, less than about 1 mm, e.g. less than about 0.7 mm, less than about 0.5 mm, or less than about 0.3 mm.

Figure 2:
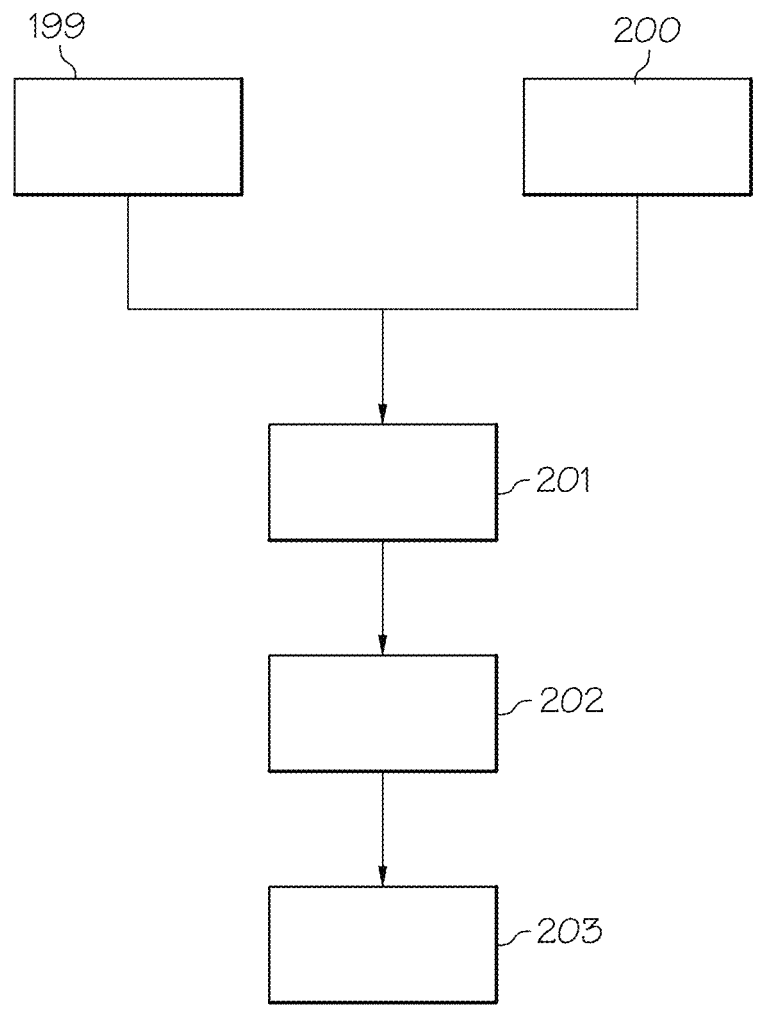
FIG. 2 is a flow chart of a method of validating edge strength of a glass sheet.

Considering now the method of validating edge strength of the glass sheet 10, as shown in FIG. 2, with reference to FIG. 1, the method can comprise a step (I) 201 of noncontactually thermally loading the glass sheet 10 to subject at least a portion 22 of the at least one edge 18 to a tensile stress. The noncontactual thermal loading of the glass sheet 10 to subject at least the portion 22 of the at least one edge 18 to a tensile stress can include generating a temperature difference between a portion 26 of the glass sheet 10 near the at least one edge 18 and the portion 22 of the at least one edge 18, such that the temperature of the portion 26 near the at least one edge 18 is greater than the temperature of the portion 22 of the at least one edge 18. The noncontactual thermal loading can be accomplished, for example, by heating the portion 26 of the glass sheet 10 near the at least one edge 18, cooling the portion 22 of the at least one edge 18, or both. This is in contrast, for example, to heating that is uniform across a glass sheet 10 and that thus would not generate a temperature difference across the glass sheet 10. Without wishing to be bound by theory, it is believed that a temperature difference between the portion 26 and the portion 22, wherein the portion 26 is at higher temperature than the portion 22, subjects the portion 26 to a compressive stress, and correspondingly subjects the portion 22 to a tensile stress. The at least a portion 22 of the at least one edge 18 can be part or all of the at least one edge 18.

Figure 3:
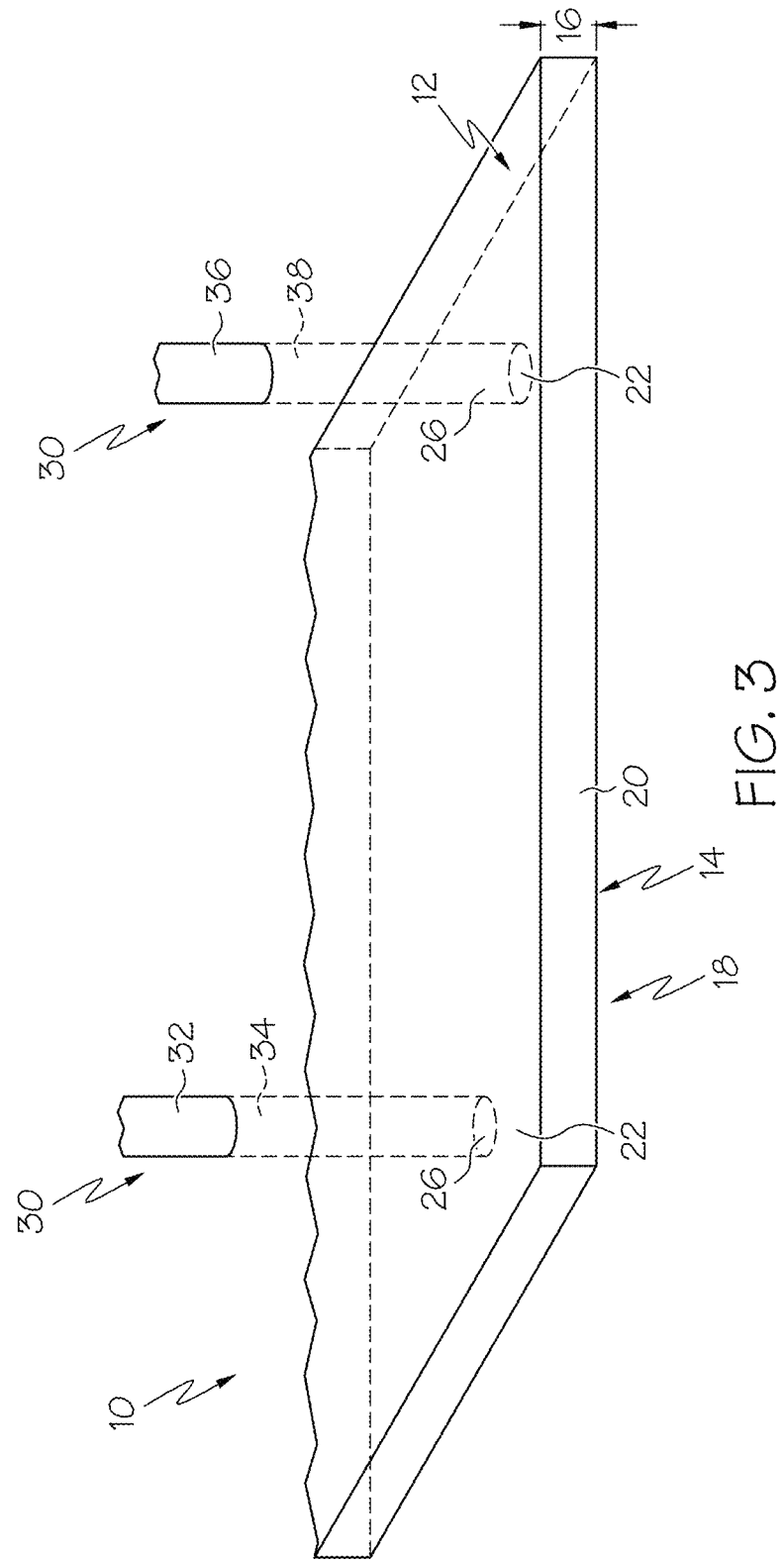
FIG. 3 is a schematic perspective view of part of an example glass sheet, also illustrating an infrared lamp and a cylinder of gas.

As shown in FIG. 3, in accordance with step (I) the noncontactual thermal loading is carried out by use of a source 30 of thermal loading that does not come in direct contact with the glass sheet 10. Exemplary approaches for such noncontactual thermal loading include use of an infrared lamp (e.g., broadband light bulb, narrowband lasers, etc.) as the source 30 of thermal loading, for example to deliver a focused infrared beam 34 to a portion 26 of the glass sheet 10 near the at least one edge 18, thereby heating the portion 26 relative to at least a portion 22 of the at least one edge 18, without the infrared lamp 32 coming in contact with the glass sheet 10. Exemplary approaches for noncontactual thermal loading also include use of a cylinder 36 of gas as the source 30 of thermal loading, for example to deliver a focused jet 38 of cold gas to at least a portion 22 of the at least one edge 18, thereby cooling the portion 22 relative to a portion 26 of the glass sheet 10 near the at least one edge 18, without the cylinder 36 coming in contact with the glass sheet 10. This is in contrast, for example, to heating a glass sheet 10 in an oven, the glass sheet 10 being on a thermally conductive rack, as this would result in thermal loading concentrated at points of contact between the rack and the glass sheet 10. This is also in contrast, for example, to cooling at least one edge 18 of a glass sheet 10 by submerging the at least one edge 18 in a cold liquid, as this would involve direct contact between the glass sheet 10 and a source 30 of thermal loading, i.e. the cold liquid. Without wishing to be bound by theory, it is believed that thermally loading the glass sheet 10 noncontactually decreases the risk that new initial flaws may be introduced at a surface of the glass sheet 10 inadvertently based on physical contact, which may otherwise result in a deleterious weakening of the glass sheet 10 and a decrease in the edge strength thereof.

Figure 4:
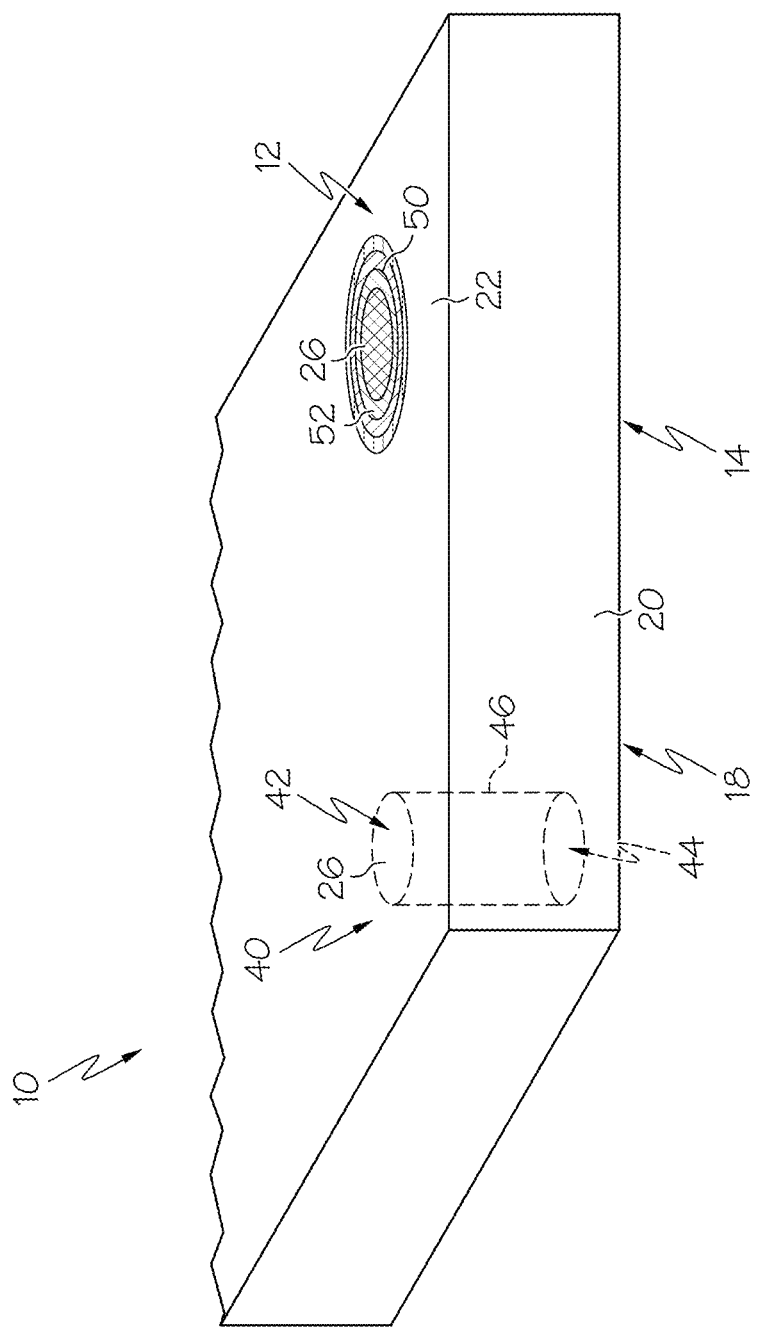
FIG. 4 is a schematic perspective view of part of an example glass sheet and illustrates that tensile stress can be a hoop stress.

As shown in FIG. 4, the tensile stress can be a hoop stress. This can be accomplished, for example, by generating a temperature difference between a portion 26 of the glass sheet 10 near the at least one edge 18 and a portion 22 of the at least one edge 18, the portion 26 being at higher temperature than the portion 22, wherein the portion 26 has the shape of a cylinder 40, the first end 42 of the cylinder being located at the first surface 12 of the glass sheet 10, the second end 44 of the cylinder being located at the second surface 14 of the glass sheet 10, and the body 46 of the cylinder extending through the glass sheet 10 therebetween, and wherein the portion 26 is located a distance from, i.e. does not intersect, the at least one edge 18. The resulting tensile stress is a hoop stress that is exerted circumferentially from the portion 26. The resulting tensile stress is also similar in part to tensile stresses to which glass sheets are subjected during typical uses, and thus can be used to validate edge strength that has a practical relevance.

As also shown in FIG. 4, step (I) can comprise producing at least one temperature gradient 50 in the glass sheet 10. The temperature gradient can be directed from a portion 26 of the glass sheet 10 near the at least one edge 18 to at least a portion 22 of the at least one edge 18, the portion 26 having a higher temperature than the portion 22, and can reflect the rate at which the temperature of the glass sheet changes therebetween. The temperature gradient 50 can, for example, emanate from a site 52 on the glass sheet 10, e.g. a spot, circle, or the like, that is heated, the site 52 being a distance from, i.e. not intersecting, the at least one edge 18. By having the temperature gradient 50 emanate from such a site 52 on the glass sheet 10, it is possible to maintain a high degree of control over the intensity and direction of the resulting tensile stress.

As shown in FIG. 5, the site 52 can, for example, have a position that changes based on translational motion of the glass sheet 10 relative to the source 30 of the noncontactual thermal loading. This can be based, for example, on the glass sheet 10 being in motion, e.g. on a conveyor 54, while the source 30 of noncontactual thermal loading is not. Alternatively, the source 30 of noncontactual thermal loading can be in motion, while the glass sheet 10 is not. As still another alternative, both the glass sheet 10 and the source 30 of noncontactual thermal loading can be in motion. In each case, the translational motion of the glass sheet 10 relative to the source 30 of the noncontactual thermal loading can provide a simple basis for subjecting at least a portion 22 of the at least one edge 18, e.g. part or all of the at least one edge 18, to a tensile stress, thereby allowing validation of edge strength with respect to the at least one edge 18. Thus, for example, during step (I), all of the at least one edge 18 can be progressively subjected to the tensile stress, based on translational motion of the glass sheet 10 relative to the source 30 of the noncontactual thermal loading. By this approach, all of the at least one edge 18 can be subjected to a peak tensile stress, thereby allowing validation of edge strength with respect to all of the at least one edge 18.

Figure 7:
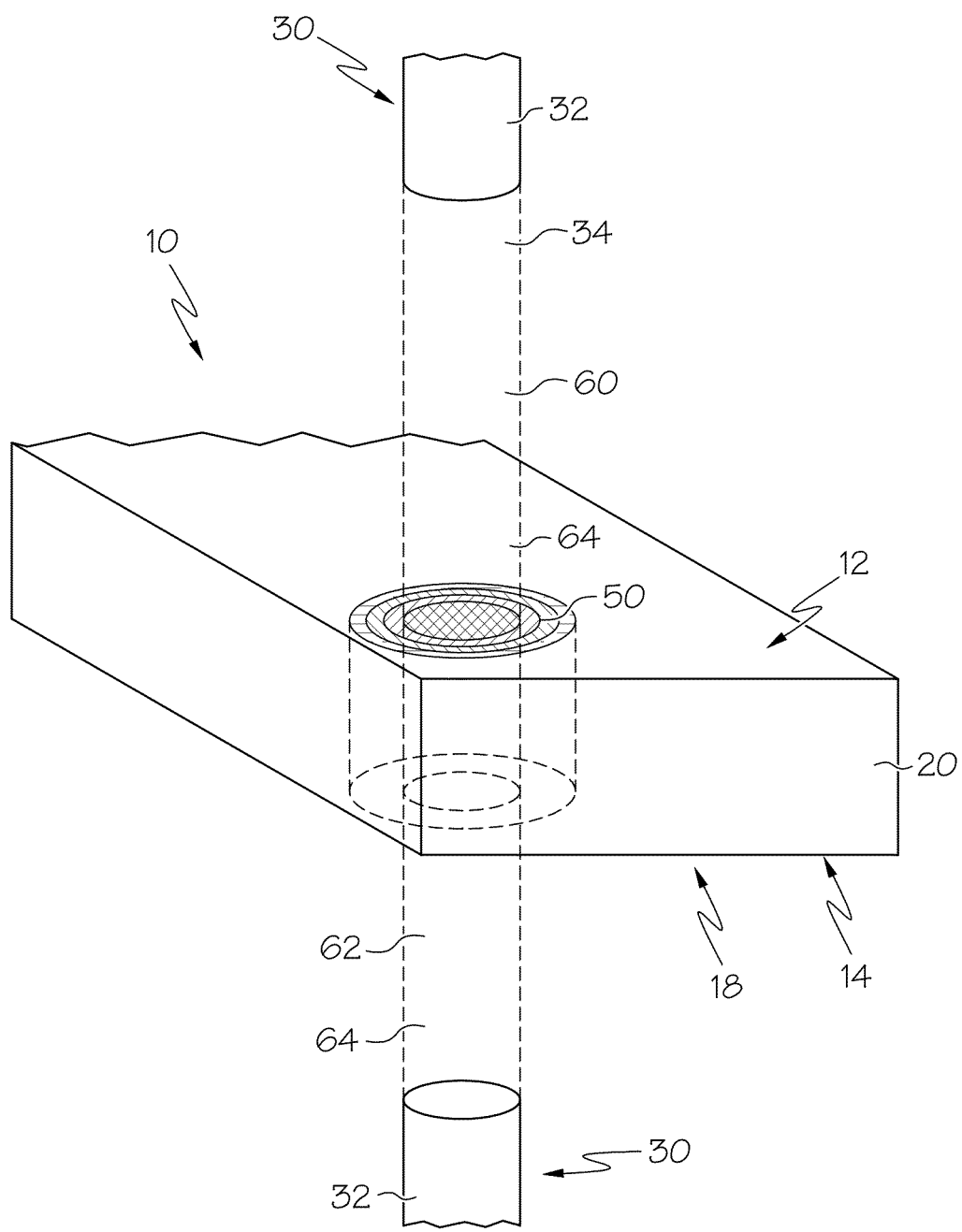
FIG. 7 is a schematic perspective view of part of an example glass sheet, also illustrating focused infrared beams and a temperature gradient.

Considering step (I) in additional detail, as shown in FIG. 7 step (I) can comprise delivering at least one focused infrared beam 34 to at least one of the first and second surfaces 12 and 14 of the glass sheet 10, the beam 34 producing at least one temperature gradient 50 in the glass sheet 10. For example, the glass sheet 10 can be positioned in the path of a focused infrared beam 34, with the first surface 12 of the glass sheet 10 proximal to the beam 34, such that the beam 34 is delivered to the glass sheet 10 at the first surface 12 thereof. Alternatively the glass sheet 10 can be positioned similarly except that the second surface 14 is proximal to the beam 34, such that the beam 34 is delivered to the glass sheet 10 at the second surface 14 thereof. Also for example, the glass sheet 10 can be oriented such that the first and/or second surfaces 12 and 14 thereof are substantially or precisely normal to the beam 34, although other orientations can also be used. By delivering the at least one focused infrared beam 34 to at least one of the first and second surfaces 12 and 14 of the glass sheet 10, the glass sheet 10 can be heated with a high degree of precision, both in terms of intensity and location, at the first and second surfaces 12 and 14 at which the beam 34 enters and exits the glass sheet 10, and internally therebetween (e.g., by conduction from the surfaces being heated by the beam), along a path defined by the path of the beam 34. For example, the focused infrared beam 34 can heat the glass sheet 10 rapidly, not just from the first and second surfaces 12 and 14 of the glass sheet 10, but also conducting from the surfaces internally, along the path of the beam 34, allowing the at least one edge 18 to be subjected to a tensile stress rapidly, not just at the first and second surfaces 12 and 14 of the glass sheet 10, but also internally with respect to the glass sheet 10.

As also shown in FIG. 7, step (I) can also comprise delivering (i) at least a first focused infrared beam 60 to the first surface 12 of the glass sheet 10 and (ii) at least a second focused infrared beam 62 to the second surface 14 of the glass sheet 10, the at least first and second focused beams 60 and 62 forming at least one pair of beams 64 that are coincident with respect to the glass sheet 10. For example, the glass sheet 10 can be positioned in the paths of both a first focused infrared beam 60 and a second focused infrared beam 62, with the first and second surfaces 12 and 14 of the glass sheet 10 proximal to the first and second beams 60 and 62, respectively, such that the first and second beams 60 and 62 are delivered to the glass sheet 10 at the first and second surfaces 12 and 14, respectively. The glass sheet 10 can also be positioned similarly, except with the first surface 12 proximal to the second beam 62, and vice versa. Similarly as above, the glass sheet 10 can be oriented such that the first and second surfaces 12 and 14 thereof are substantially or precisely normal to the first and second beams 60 and 62, and particularly such that the first and second beams 60 and 62 form a pair of beams 64 that are coincident, e.g. entirely overlapping, with respect to the glass sheet 10. By so delivering the first and second focused infrared beams 60 and 62 to the first and second surfaces 12 and 14 of the glass sheet 10, the glass sheet 10 can be heated with an even higher degree of precision, at the first and second surfaces 12 and 14 at which the beams 60 and 62 enter and exit the glass sheet 10, and internally therebetween, along a path defined by the path of the pair of beams 64. For example, the pair of infrared beams 64 can heat the glass sheet 10 not just rapidly, but also symmetrically, with respect to the first and second surfaces 12 and 14, along the path of the pair of beams 64, allowing the at least one edge 18 to be subjected to a tensile stress not just rapidly, but also with a high degree of stress uniformity.

Figure 8:
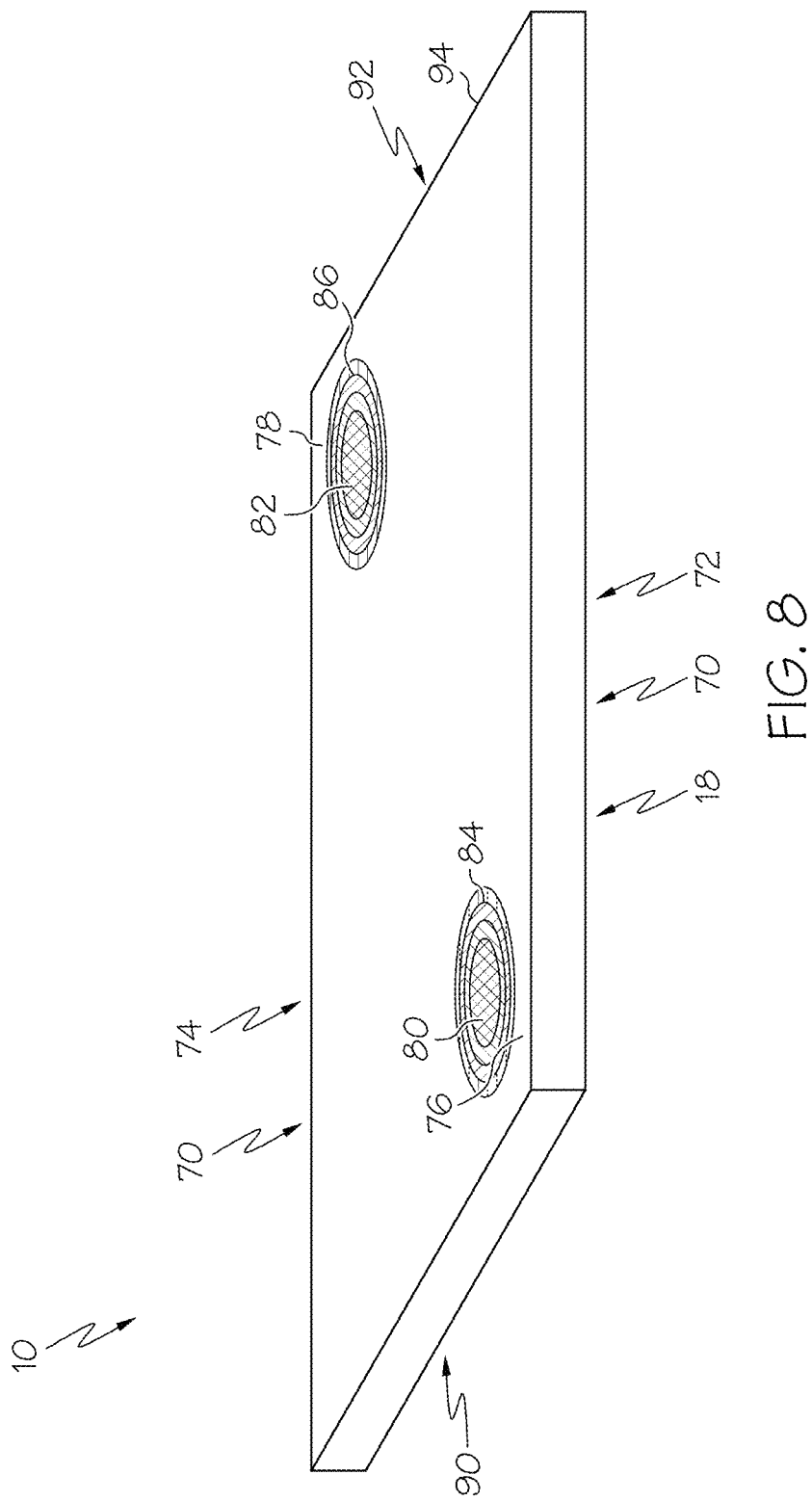
FIG. 8 is a schematic perspective view of an example glass sheet, also illustrating two temperature gradients.

As shown in FIG. 8, the method of validating edge strength of the glass sheet 10 can also be carried out with respect to a glass sheet 10 comprising a plurality of edges 70, e.g. by validating edge strength along two or more of the plurality of edges 70. For example, the method can be carried out wherein the at least one edge 18 comprises at least a first edge 72 and a second edge 74 opposing the first edge 72, and further wherein step (I) comprises independently noncontactually thermally loading the glass sheet 10 to subject at least a portion 76 of the first edge 72 and at least a portion 78 of the second edge 74 to the tensile stress. In accordance with this example, step (I) can comprise noncontactually thermally loading the glass sheet 10 to subject the first edge 72 to a first tensile stress, and independently, e.g. previously, subsequently, or simultaneously and separately, noncontactually thermally loading the glass sheet 10 to subject the second edge 74 to a second tensile stress. This can be accomplished, for example, by heating a first portion 80 of the glass sheet 10 near the first edge 72 and heating a second portion 82 of the glass sheet 10 near the second edge 74, thus creating a first temperature gradient 84 with respect to the first edge 72 and a second temperature gradient 86 with respect to the second edge 74, the heating being carried out for example by use of pairs of infrared lamps 32 to generate pairs of focused infrared beams 64, each pair of beams 64 being coincident with respect to the glass sheet 10. This can also be accomplished, for example, by cooling at least a portion 76 of the first edge 72 and cooling at least a portion 78 of the second edge 74, the cooling being carried out for example by use of jets 38 of gas. This can also be accomplished by a combination of these approaches, among others. In each case, the first and second tensile stresses can be of the same magnitude or of different magnitudes, as appropriate. In addition, the noncontactual thermal loading can be carried out to subject additional edges 70 of the glass sheet 10, e.g. a third edge 90 and a fourth edge 92 opposing the third edge 90, to the tensile stress independently. Furthermore, translational motion of the glass sheet 10 relative to the sources 30 of the noncontactual thermal loading can be carried out to subject as much as all of the edges 70 to the tensile stress. Thus, for example, the method can be carried out wherein the at least one edge 18 comprises a complete perimeter 94 of the glass sheet 10, and further wherein step (I) comprises noncontactually thermally loading the glass sheet 10 to subject the complete perimeter 94 to the tensile stress.

As can be seen in FIG. 3, step (I) can also comprise delivering at least one focused jet 38 of gas along a portion 22 of the at least one edge 18, the gas being colder than the at least one edge, the gas producing at least one temperature gradient in the glass sheet 10. The gas can be, for example, nitrogen vapor obtained by evaporation of liquid nitrogen, among others, and can be directed specifically at the at least one edge 18, e.g. by use of a nozzle.

As shown in FIG. 2, with reference to FIG. 1 and FIG. 6, the method of validating edge strength of the glass sheet 10 can also comprise a step (II) 202 of determining whether the at least one edge 18 has an edge strength below a predetermined level by detecting whether a resulting strength imperfection 28 has originated in the glass sheet 10 due to the noncontactual thermal loading of step (I). As noted above, strength imperfections 28 can originate from initial flaws 29 when a glass sheet 10 is subjected to tensile stress, and accordingly initial flaws 29 can compromise the strength of the glass sheet 10. More particularly, when at least one edge 18 of a glass sheet 10 that includes an initial flaw 29 is subjected to a tensile stress, such as based on the noncontactual thermal loading of step (I), a resulting strength imperfection 28 can originate in the glass sheet 10 from the initial flaw 29. The resulting strength imperfection 28 can be a crack, fissure, fracture, breakage, or the like, can vary from microscopic to macroscopic in scale, and can further degrade edge strength of the glass sheet 10 relative to initial flaw 29, resulting for example in cracking and/or breaking of the glass sheet 10. The resulting strength imperfection will form if at least one edge 18 of the glass sheet 10 is subjected to a tensile stress that exceeds the corresponding edge strength, and will do so essentially immediately or very soon after formation of the temperature gradient. Also, the tensile strength to which the at least one edge 18 is subjected can be controlled to match a corresponding edge strength of a predetermined level. The edge strength of a predetermined level can be, for example, an edge strength that is expected for the glass sheet 10 (e.g. based on its composition and dimensions in the absence of any initial flaws 29, and/or considering edge grinding or other edge finishing processes performed on the edge of the glass) and edge strength that is desired for the glass sheet 10, e.g. based on testing new compositions for improved edge strengths, and/or an edge strength that is required for the glass sheet 10, e.g. based on subsequent intended uses of the glass sheet 10. Accordingly, detection of the presence of a resulting strength imperfection 28 following the noncontactual thermal loading of step (I) can be indicative of the at least one edge 18 having an edge strength below a predetermined level. Conversely, the absence of a resulting strength imperfection 28 following the noncontactual thermal loading of step (I) can be indicative of the at least one edge 18 not having an edge strength below a predetermined level.

Figure 9:
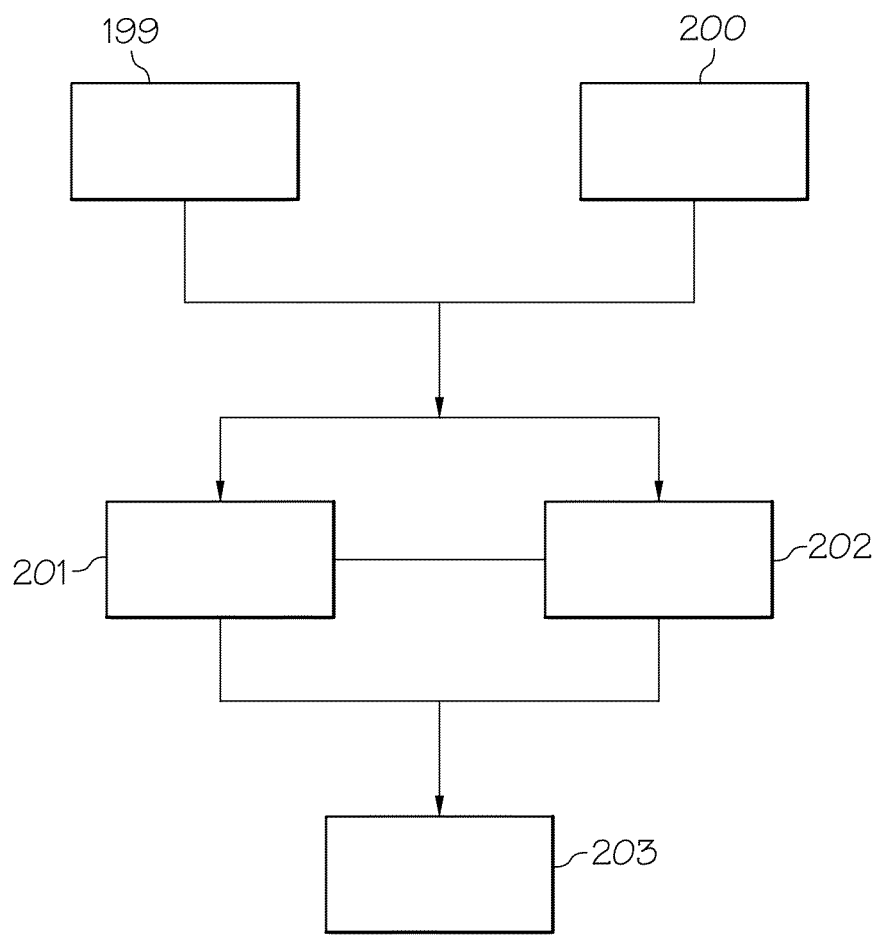
FIG. 9 is a flow chart of a method of validating edge strength of a glass sheet.

Considering step (II) in more detail, as shown in FIG. 6 the detecting of the resulting strength imperfection 28 can comprise, for example, visual detection 120, optical detection 122, or acoustic detection 124. Visual detection 120 can be done manually, e.g. based on an individual inspecting a glass sheet 10 for a resulting strength imperfection 28 that is on a macroscopic scale, e.g. following step (I), as shown in FIG. 2. In further examples, magnifying lenses may be used to help allow visual inspection. Optical detection 122 can be done automatically, e.g. based on measurement of refraction and/or reflection patterns of glass sheets 10 and corresponding electronic processing to identify those refraction patterns that are aberrant due to the presence of a resulting strength imperfection 28, e.g. during step (I), as shown in FIG. 9, or following step (I), as shown in FIG. 2. Acoustic detection 124 can also be done manually, e.g., based on an individual listening to the glass sheet 10 for noises typical of strength imperfection formation. Acoustic detection 124 can also be carried out automatically, e.g. based on use of a microphone to detect sounds generated during origination of a resulting strength imperfection 28, e.g. during step (I), as shown in FIG. 9. Automatic acoustic monitoring can have the advantage of detecting sounds with frequencies that may be outside of the audible range of a human, thereby possibly making manual acoustic detection undesirable in example applications.

As shown in FIG. 2 and FIG. 9, the method of validating edge strength of the glass sheet 10 can also comprise a step (III) 203 of estimating the tensile stress based on an interference fit model of a heated inner cylinder and a non-heated outer cylinder. In accordance with this model, the inner cylinder corresponds to a site on a glass sheet from which a temperature gradient emanates and has an inner ring radius. The outer cylinder corresponds to a portion of the glass sheet surrounding the site and comprises an outer edge that intersects the at least one edge of the glass sheet and has an outer ring radius. The inner and outer cylinders are concentric and made from the glass sheet. The tensile stress is estimated in accordance with the equation:

$$s_t = +\Delta T \alpha E(a^2/b^2)$$

in which $s_t$ is the tangential stress at the outer edge of the outer cylinder; $\Delta T$ is the temperature difference between the inner cylinder and the outer cylinder; $\alpha$ is the coefficient of thermal expansion of the glass sheet; E is the Young's modulus for the glass sheet; a is the inner ring radius of the inner cylinder; and b is the outer ring radius of the outer cylinder.

This interference fit model can be used to estimate tensile stress during noncontactual thermal loading of the glass sheet. For example, for noncontactual thermal loading of a glass sheet based on use of a focused infrared beam, the inner ring radius of the inner cylinder can be fixed or varied, e.g. by fixing or varying the diameter of the infrared beam. The outer ring radius of the outer cylinder also can be fixed or varied, e.g. by fixing or varying the position of the infrared beam relative to the at least one edge. The temperature difference between the inner cylinder and the outer cylinder also can be fixed or varied, e.g. by fixing or varying the intensity of an infrared beam used to heat a part of the glass sheet near the at least one edge of the glass sheet. The coefficient of thermal expansion of the glass sheet and the Young's modulus for the glass sheet depend on the composition of the glass sheet. The interference fit model thus can be used to estimate tensile stress during a specific set of conditions, e.g. fixed $\Delta T$, a, and b, or under a range of conditions, e.g. varying $\Delta T$, a, and/or b. The interference fit model can also be used to match the noncontactual thermal loading of a particular glass sheet with the edge strength expected, desired, or required for the glass sheet, e.g. by ensuring that the noncontactual thermal loading is appropriate to subject the at least one edge of the glass sheet to a tensile stress that can cause a resulting strength imperfection to originate in the glass sheet if the at least one edge has an edge strength below a predetermined level.

The method of validating edge strength of the glass sheet 10 can be applied during manufacture of glass sheets 10, e.g. for purposes of quality control. For example, as shown in FIG. 2 and FIG. 9 the method can further comprise a step 199 of shaping the at least one edge 18 of the glass sheet 10 prior to steps (I) and (II), wherein the glass sheet 10 is of a predetermined size. As noted above, cutting, edge machining, and other processing steps can introduce initial flaws 29, such as chips or cracks, at surfaces and edges of the glass sheet. By carrying out steps (I) and (II) subsequent to shaping the at least one edge 18 of the glass sheet 10 during manufacture, the glass sheet 10 can be subjected to immediate and efficient edge strength proof testing. The method also can further comprise a step 200 of chemically strengthening the glass sheet 10 prior to steps (I) and (II). By carrying out steps (I) and (II) subsequent to chemically strengthening the glass sheet 10, the effectiveness of the chemical strengthening in particular can be confirmed. The method also can be applied to validate edge strength of pluralities of glass sheets 10 corresponding to a production batch, e.g. all of the glass sheets 10 that have been manufactured in a particular production run, cut to a particular predetermined size, and finished, for purposes of immediate and efficient edge strength proof testing based not on statistical sampling but rather direct testing of each glass sheet 10.

Figure 10:
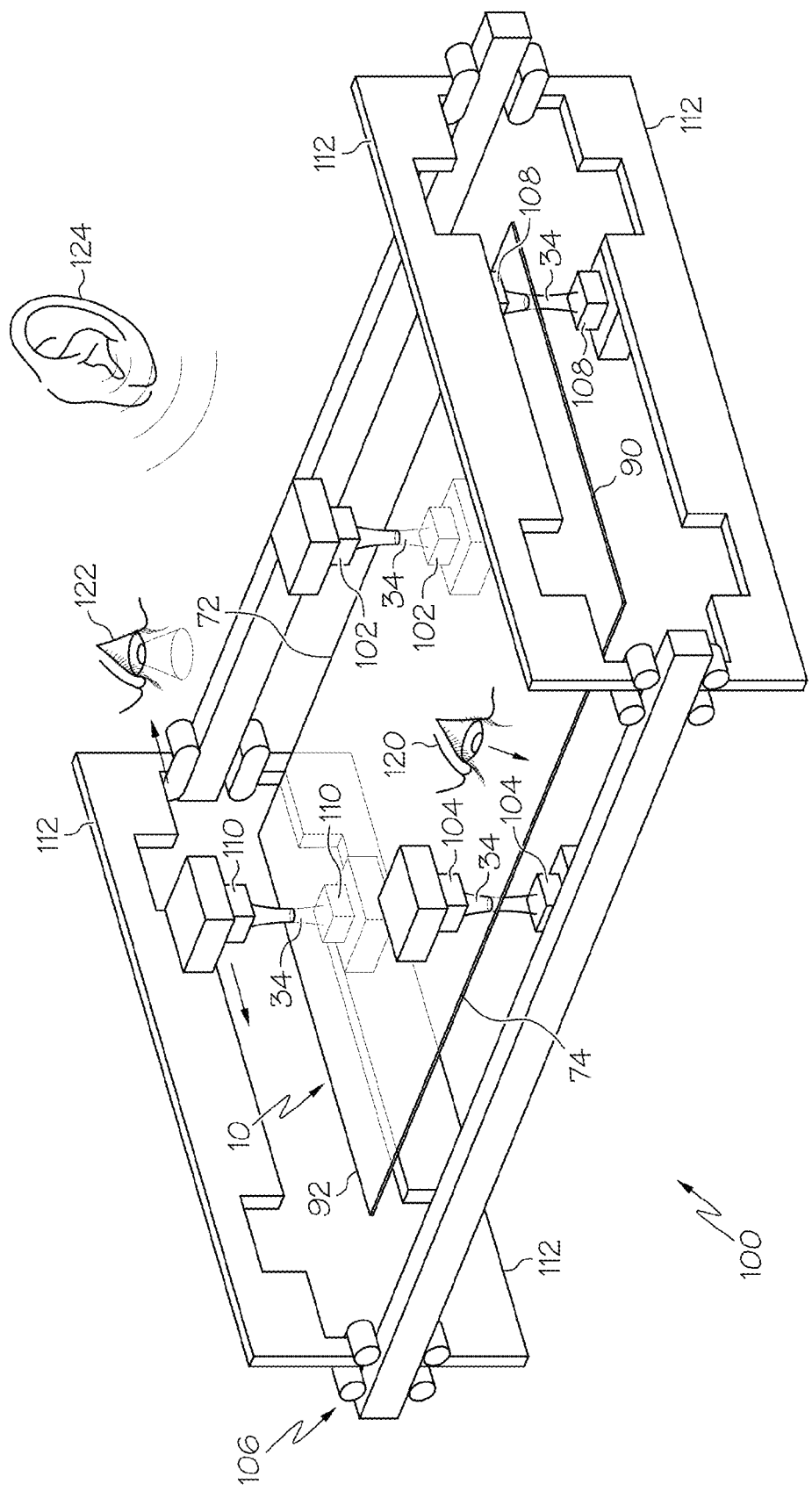
FIG. 10 is a schematic perspective view of an exemplary apparatus that can be used to validate edge strength of a glass sheet.

As shown in FIG. 10, an exemplary apparatus 100 can be used to validate edge strength during manufacture of glass sheets 10, e.g. downstream from an edge finishing station, and to do so with respect to the entire perimeter 94 of a glass sheet 10 having four edges 72, 74, 90, and 92. The apparatus 100 can comprise first and second pairs of stationary infrared lamps 102 and 104 and a conveyor 106 for glass sheets 10, one member of each of the first and second pairs of infrared lamps 102 and 104 above the conveyor 106 and the other member of each of the first and second pairs of infrared lamps 102 and 104 below. The apparatus 100 can also comprise third and fourth pairs of mobile infrared lamps 108 and 110 based on attachment thereof to gantries 112, again with one member of each of the first and second pairs of infrared lamps 108 and 110 above the conveyor 106 and the other member of each of the first and second pairs of infrared lamps 108 and 110 below. As the glass sheet 10 translates along the conveyor 106, the first and second edges 72 and 74 of the glass sheet 10 that are oriented parallel to the direction of translation of the glass sheet 10 are noncontactually thermally loaded by infrared beams 34 from the first and second pairs of stationary infrared lamps 102 and 104, respectively, as discussed above. Moreover, the third and fourth edges 90 and 92 of the glass sheet 10 that are oriented normal to the direction of translation of the glass sheet 10 are noncontactually thermally loaded by infrared beams 34 from the third and fourth pairs of mobile infrared lamps 108 and 110, respectively, based on the conveyors 106 moving translationally in sequence with, but perpendicular to, the translational motion of the glass sheet 10. The intensity of pairs of infrared lamps 102, 104, 108, and 110, can be adjusted as a function of speed of translation of the glass sheet 10 to achieve heating of portions of the glass sheet 10 near the edges 72, 74, 90, and 92 to desired peak temperatures by the infrared beams 34, resulting in a corresponding peak tensile stress on the edges 72, 74, 90, and 92 of the glass sheet 10. Peak tensile stress can be adjusted in order to define edge failure stress probability distributions as a function of edge processing conditions. Once probability distributions are known, the apparatus 100 can be set to monitor additional glass sheets 10 to assure product quality.

Alternatives, such as an apparatus that includes pairs of first and second stationary infrared lamps 102 and 104 but not the pairs of third and fourth mobile infrared lamps 108 and 110 can also be used to validate edge strength along the entire perimeter 94 of a glass sheet 10 having four edges 72, 74, 90, and 92, for example by using the apparatus to validate edge strength with respect to the first and second edges 72 and 74 of the glass sheet 10, then rotating the glass sheet 10 by 90° with respect to the apparatus, and then using the apparatus to validate edge strength with respect to the third and fourth edges 90 and 92 of the glass sheet 10.

EXAMPLES

Figure 11:
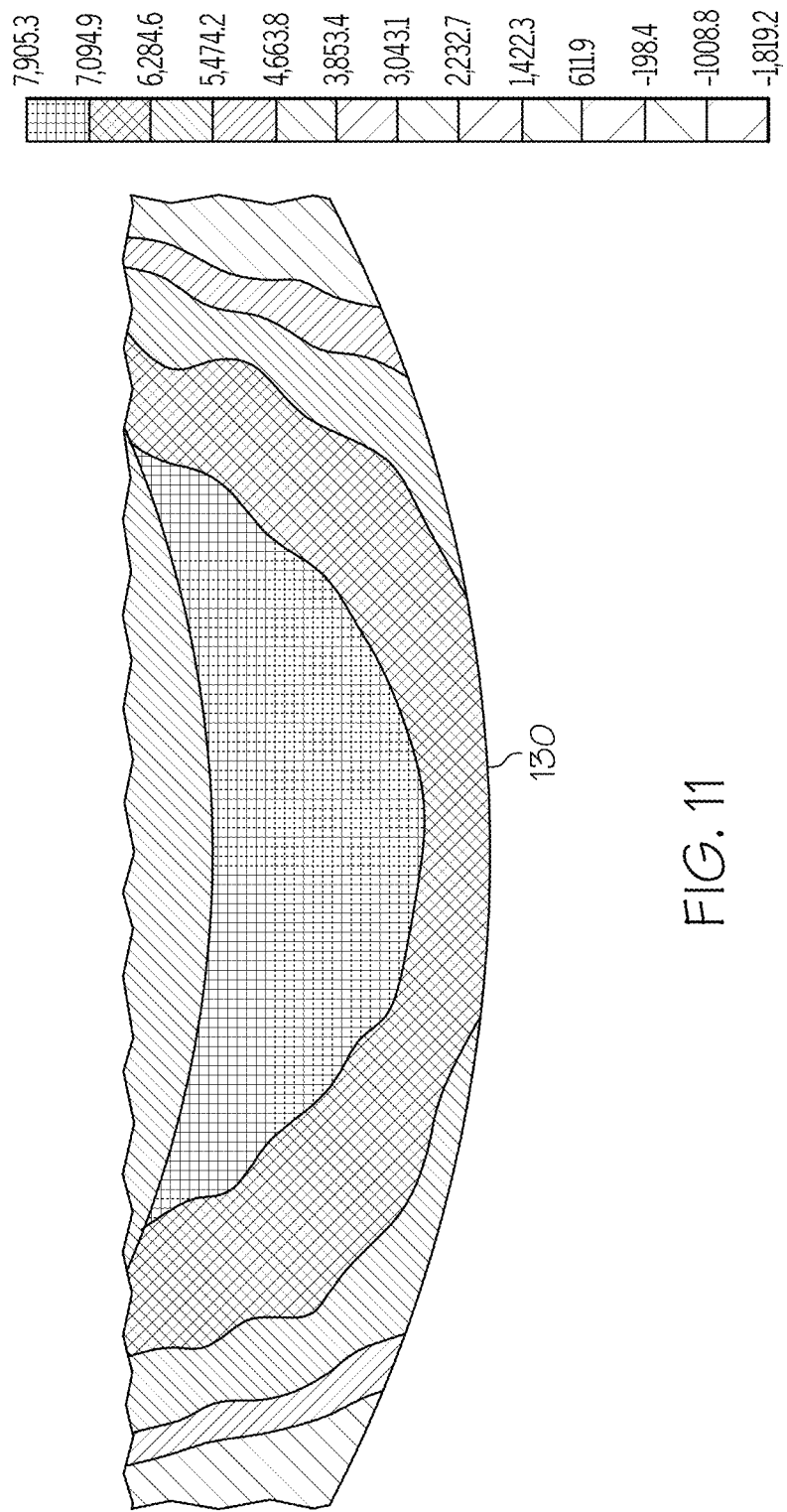
FIG. 11 is a diagram of compressive and tensile stress in psi induced following heating of an internal 0.8 inch (2 cm) diameter circular region of a 1.0 inch (2.54 cm) diameter disk to a temperature of 300° C. above that of the outer ring, in accordance with a finite-element thermomechanical model.

The physical basis for thermal loading of a glass sheet can be quantitatively described by formulas that can be derived from the general case of concentric cylinders with an interference fit, i.e. an interference fit model. In accordance with the general case, the interference is generated between an inner cylinder at an elevated temperature which thermally expands and is constrained by an outer cylinder at a cooler temperature. The result is to create compressive tangential stress in the inner cylinder and tensile tangential stress in the outer cylinder, as shown with respect to a finite-element thermomechanical model in FIG. 11.

The tangential stress at the outer edge of the outer ring can be described by the following equation:

$$s_t = +\Delta T \alpha E (a^2/b^2)$$

where $s_t$ is the tangential stress (e.g. psi) at the outer edge of the outer ring; $\Delta T$ (e.g. °C.) is the temperature difference between the central and surrounding areas; $\alpha$ is the coefficient of thermal expansion (e.g. °C.$^{-1}$) of the glass sheet; E is the Young's modulus (e.g. psi) for the glass sheet; a is the inner heated ring radius (e.g. inches); and b is the outer ring radius (e.g. inches). Per convention, stresses in tension are assigned a positive value while those in compression are assigned a negative value.

The interference fit model can be used to estimate the tensile stress to which an edge of glass sheet is subjected as shown in the following example. A 1.0-inch diameter, 0.7-millimeter thick disk of CORNING® EAGLE XG™ alkaline earth boro-aluminosilicate glass has a centered circular portion having a diameter of 0.8 inches (2 cm) heated to a temperature of 300° C. above that of its outer rim. The coefficient of thermal expansion $\alpha$ is $31.7 \times 10^{-7}$ °C.$^{-1}$ and the Young's modulus E is $10.7 \times 10^6$ psi ($7.5 \times 10^5$ kgf/cm$^2$). According to the interference fit model, the cool outer edge of the disk will be under a tensile tangential stress of about 6,512 psi (457.8 kgf/cm$^2$). Those parameters applied to the finite-element thermomechanical model predicted 6,247 psi (439.2 kgf/cm$^2$), in good agreement.

Figure 12:
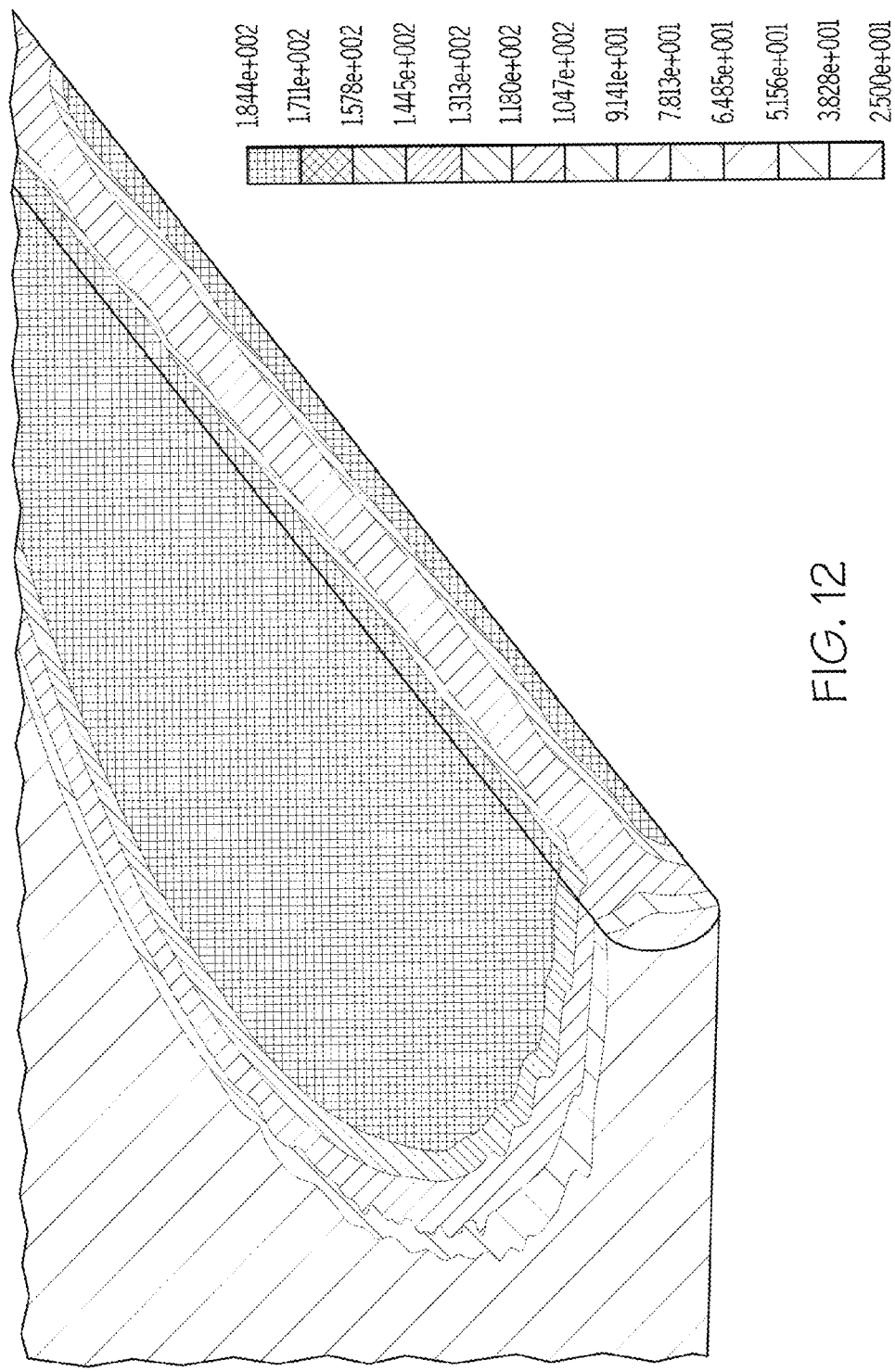
FIG. 12 is a diagram of temperature distribution in ° C. of a glass sheet at 0.5 seconds after 35 watts have been absorbed on each side of the glass sheet, near a bull-nose edge thereof, with temperatures rising from a base of 25° C. to a maximum of 184° C.
Figure 13:
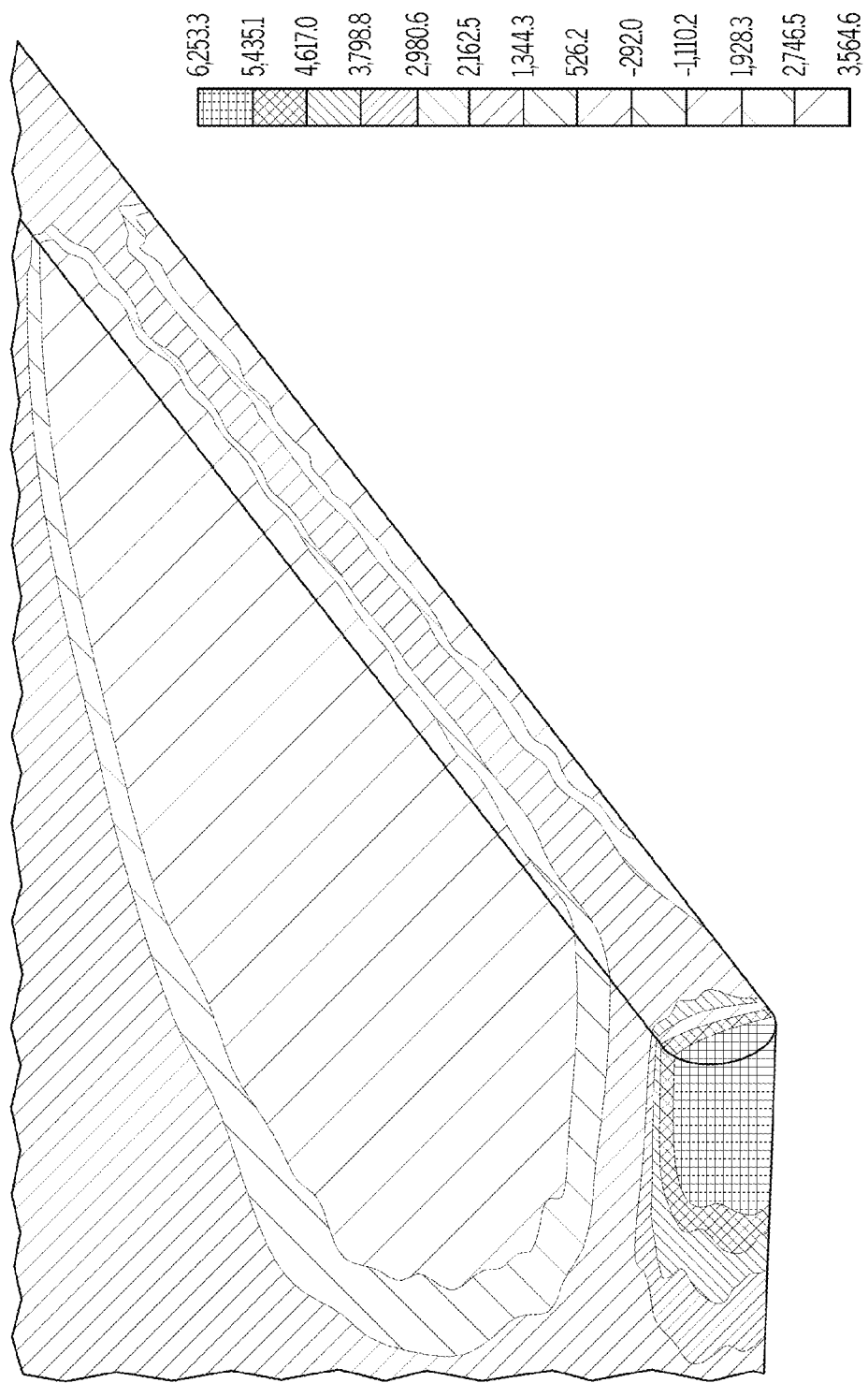
FIG. 13 is a diagram of compressive and tensile stress in psi induced in the glass sheet as described in FIG. 12, based on the temperature distribution thereof at 0.5 seconds after 35 watts have been absorbed on each side of the glass sheet, in accordance with a finite-element thermomechanical model.

To first approximation the stress formula for the circular geometry of the disk example can be applied to portions of a rectangular glass sheet. FIG. 12 illustrates a heated circular region of a glass sheet next to its edge, as a diagram of temperature distribution of the glass sheet at 0.5 seconds after 35 watts have been absorbed on each side of the glass sheet, near a bull-nose edge thereof, with temperatures rising from a base of 25° C. to a maximum of 184° C. FIG. 13 illustrates the resulting compressive and tensile stress, in accordance with a finite-element thermomechanical model. The equation above provides an estimate of the tensional stress load at the edge similar to that modeled in FIG. 13, 5,390 psi (379 kgf/cm$^2$) versus 6,250 psi (439.4 kgf/cm$^2$), respectively.

An infrared lamp with optics to focus its output beam down to a spot of a particular size can be used to heat a circular portion of the glass. If two such systems are located on either side of the glass sheet so that the spots are coincident upon the same glass area, fast and uniform heating through the thickness of the glass is possible. Temperature rise in the heated portion of glass will depend upon the lamp output power, the spectral power density of the lamp through the infrared wavelength interval, the absorption spectrum of the glass material through the same infrared wavelength interval, and the time of exposure. Of these four variables, the two of lamp output power and exposure time are easily varied and so these become the primary controls in order to achieve a specific temperature, and thus stress, rise.

The methods disclosed herein can provide an efficient and non-destructive validation of edge strength of a glass sheet. Noncontactually thermally loading the glass sheet allows loading of at least one edge of a glass sheet with a desired level of tensile stress, thus providing a validation of edge strength of at least part of the at least one edge. Moreover, when coupled with translational motion of the glass sheet relative to a source of the noncontactual thermal loading, all of the at least one edge of the glass sheet can be progressively subjected to the tensile stress, thus providing a validation of edge strength of all of the at least one edge. In addition, where the at least one edge comprises a complete perimeter of the glass sheet, a validation of the edge strength of the complete perimeter can be obtained. Furthermore, determining whether the at least one edge has an edge strength below a predetermined level by detecting whether a resulting strength imperfection has originated in the glass sheet due to the noncontactual thermal loading provides a proof-test for edge strength, such that if no resulting strength imperfection has originated, it can be concluded that the strength of the edge is sufficiently high. When carried out as part of a glass production system, the methods allow for exposure of every glass sheet to a desired level of stress for purposes of real-time process feedback and product quality assurance, without destruction of the glass sheets having an edge strength that is sufficiently high. The methods thus can provide beneficial real-time feedback into the edge finishing process.

It will be apparent to those skilled in the art that various modifications and variations can be made to the present disclosure without departing from the spirit and scope of the invention. Thus, it is intended that the present invention cover the modifications and variations of this disclosure provided they come within the scope of the appended claims and their equivalents.

What is claimed is:

1. A method of validating edge strength of a glass sheet comprising a first surface, a second surface opposing the first surface, a thickness defined between the first surface and the second surface, and at least one edge comprising an edge surface, wherein the first surface and the second surface intersect the edge surface of the at least one edge, the method comprising the steps of:
   (I) noncontactually thermally loading the glass sheet to subject at least a portion of the at least one edge to a tensile stress corresponding to an edge strength at a predetermined level; and
   (II) determining whether the at least one edge has an edge strength below the predetermined level by detecting whether a resulting strength imperfection has originated in the glass sheet due to the noncontactual thermal loading of step (I).

2. The method of claim 1, wherein the tensile stress is a hoop stress.

3. The method of claim 1, wherein step (I) comprises producing at least one temperature gradient in the glass sheet.

4. The method of claim 1, wherein step (I) comprises producing at least one temperature gradient in the glass sheet, the temperature gradient emanating from a site on the glass sheet, the site being a distance from the edge surface.

5. The method of claim 1, wherein step (I) comprises producing at least one temperature gradient in the glass sheet, the temperature gradient emanating from a site on the glass sheet, the site having a position that changes based on translational motion of the glass sheet relative to a source of the noncontactual thermal loading.

6. The method of claim 1, wherein step (I) comprises delivering at least one focused infrared beam to at least one of the first and second surfaces of the glass sheet, the beam producing at least one temperature gradient in the glass sheet.

7. The method of claim 1, wherein step (I) comprises delivering (i) at least a first focused infrared beam to the first surface of the glass sheet and (ii) at least a second focused infrared beam to the second surface of the glass sheet, the at least first and second focused beams forming at least one pair of beams that are coincident with respect to the glass sheet.

8. The method of claim 1, wherein during step (I) all of the at least one edge is progressively subjected to the tensile stress based on translational motion of the glass sheet relative to a source of the noncontactual thermal loading.

9. The method of claim 1, wherein the at least one edge comprises at least a first edge and a second edge opposing the first edge, and further wherein step (I) comprises independently noncontactually thermally loading the glass sheet to subject at least a portion of the first edge and at least a portion of the second edge to the tensile stress.

10. The method of claim 1, wherein the at least one edge comprises a complete perimeter of the glass sheet, and further wherein step (I) comprises noncontactually thermally loading the glass sheet to subject the complete perimeter to the tensile stress.

11. The method of claim 1, wherein step (I) comprises delivering at least one focused jet of gas to at least a portion of the at least one edge, the gas being colder than the at least one edge, the gas producing at least one temperature gradient in the glass sheet.

12. The method of claim 1, wherein during step (II) the detecting of the resulting imperfection comprises a detection method selected from the group consisting of visual detection, optical detection, and acoustic detection.

13. The method of claim 1, further comprising a step (III) of estimating the tensile stress based on an interference fit model of a heated inner cylinder and a non-heated outer cylinder, wherein:
the inner cylinder corresponds to a site on the glass sheet from which a temperature gradient emanates and has an inner ring radius;
the outer cylinder corresponds to a portion of the glass sheet surrounding the site and comprises an outer edge that intersects the at least one edge of the glass sheet and has an outer ring radius;
the inner and outer cylinders being concentric and made from the glass sheet,
in accordance with the equation:

$$s_t = +\Delta T \alpha E (a^2/b^2)$$

in which $s_t$ is the tangential stress at the outer edge of the outer cylinder; $\Delta T$ is the temperature difference between the inner cylinder and the outer cylinder; $\alpha$ is the coefficient of thermal expansion of the glass sheet; $E$ is the Young's modulus for the glass sheet; $a$ is the inner ring radius of the inner cylinder; and $b$ is the outer ring radius of the outer cylinder.

14. The method of claim 1, further comprising a step of shaping the at least one edge of the glass sheet prior to steps (I) and (II), wherein the glass sheet is of a predetermined size.

15. The method of claim 1, further comprising a step of chemically strengthening the glass sheet prior to steps (I) and (II).

16. The method of claim 1, wherein the thickness defined between the first surface of the glass sheet and the second surface of the glass sheet is less than about 1 mm.

17. A method of validating edge strength of a glass sheet comprising a first surface, a second surface opposing the first surface, a thickness defined between the first surface and the second surface, and at least one edge comprising an edge surface, wherein the first surface and the second surface intersect the edge surface of the at least one edge, the method comprising the steps of:
(I) noncontactually thermally loading the glass sheet to produce at least one temperature gradient in the glass sheet, the temperature gradient emanating from a site on the glass sheet located a distance from the edge surface, the site having a position that changes based on translational motion of the glass sheet relative to a source of the noncontactual thermal loading, wherein the temperature gradient subjects at least a portion of the at least one edge to a tensile stress; and
(II) determining whether the at least one edge has an edge strength below a predetermined level by detecting whether a resulting strength imperfection has originated in the glass sheet due to the noncontactual thermal loading of step (I).

18. The method of claim 17, wherein step (I) comprises delivering at least one focused infrared beam to at least one of the first and second surfaces of the glass sheet, the beam producing at least one temperature gradient in the glass sheet.

19. The method of claim 17, wherein step (I) comprises delivering (i) at least a first focused infrared beam to the first surface of the glass sheet and (ii) at least a second focused infrared beam to the second surface of the glass sheet, the at least first and second focused beams forming at least one pair of beams that are coincident with respect to the glass sheet.

20. The method of claim 17, wherein step (I) comprises delivering at least one focused jet of gas to at least a portion of the at least one edge, the gas being colder than the at least one edge, the gas producing at least one temperature gradient in the glass sheet.

* * * * *